(12) United States Patent
Trooskens et al.

(10) Patent No.: US 11,699,504 B2
(45) Date of Patent: *Jul. 11, 2023

(54) HASH-BASED EFFICIENT COMPARISON OF SEQUENCING RESULTS

(71) Applicant: SHARECARE AI, INC., Palo Alto, CA (US)

(72) Inventors: Geert Trooskens, Ghent (BE); Wim Maria R. Van Criekinge, Waarloos (BE)

(73) Assignee: SHARECARE AI, INC., Palo Alto, CA (US)

(*) Notice: Subject to any disclaimer, the term of this patent is extended or adjusted under 35 U.S.C. 154(b) by 743 days.

This patent is subject to a terminal disclaimer.

(21) Appl. No.: 16/575,276

(22) Filed: Sep. 18, 2019

(65) Prior Publication Data

US 2020/0098446 A1 Mar. 26, 2020

Related U.S. Application Data

(60) Provisional application No. 62/734,840, filed on Sep. 21, 2018, provisional application No. 62/734,872, (Continued)

(51) Int. Cl.
*G06F 16/00* (2019.01)
*G16B 30/00* (2019.01)
*G16B 40/00* (2019.01)
*G16B 10/00* (2019.01)
*G06F 16/22* (2019.01)
(Continued)

(52) U.S. Cl.
CPC ........... *G16B 30/00* (2019.02); *C12Q 1/6827* (2013.01); *C12Q 1/6869* (2013.01); *G06F 16/2255* (2019.01); *G06F 17/18* (2013.01); *G16B 5/00* (2019.02); *G16B 10/00* (2019.02); *G16B 20/20* (2019.02); *G16B 20/40* (2019.02); (Continued)

(58) Field of Classification Search
None
See application file for complete search history.

(56) References Cited

U.S. PATENT DOCUMENTS

| 7,797,323 B1 * | 9/2010 | Eshghi ................. G06F 16/1748 707/747 |
| 2014/0272951 A1 | 9/2014 | Chakravarti et al. |
| 2017/0177597 A1 | 6/2017 | Asimenos |

OTHER PUBLICATIONS

Benedikt Elser, Mar. 2006. Institut Fur Informatik Managing Trust in a Distributed Network, pp. 1-80.*
(Continued)

*Primary Examiner* — Tuankhanh D Phan
(74) *Attorney, Agent, or Firm* — Haynes Beffel & Wolfeld LLP; Ernest J. Beffel, Jr.; Korbin S Van Dyke

(57) ABSTRACT

The technology disclosed generates a reference array of variant data for locations that are shared between read results which are to be compared, and generates hashes over a selected pattern length of positions in the reference array to independently produce non-unique window hashes for base patterns in the read results. It then selects for comparison window hashes that occur less than a ceiling number of times and compares the selected window hashes to identify common window hashes between the read results. It then determines a similarity measure for the read results based on the common window hashes.

27 Claims, 14 Drawing Sheets
(5 of 14 Drawing Sheet(s) Filed in Color)

Related U.S. Application Data filed on Sep. 21, 2018, provisional application No. 62/734,895, filed on Sep. 21, 2018.

(51) Int. Cl.
| | |
|---|---|
| *G16B 20/20* | (2019.01) |
| *G16B 45/00* | (2019.01) |
| *G16B 20/40* | (2019.01) |
| *G16B 5/00* | (2019.01) |
| *G16B 40/10* | (2019.01) |
| *C12Q 1/6827* | (2018.01) |
| *C12Q 1/6869* | (2018.01) |
| *G06F 17/18* | (2006.01) |
| *G16B 50/00* | (2019.01) |

(52) U.S. Cl.
CPC ............ *G16B 40/00* (2019.02); *G16B 40/10* (2019.02); *G16B 45/00* (2019.02); *G16B 50/00* (2019.02)

(56) References Cited

OTHER PUBLICATIONS

U.S. Appl. No. 16/575,277, filed Sep. 18, 2019, US-2020-0098447-A1, Mar. 26, 2020, Pending.
U.S. Appl. No. 16/575,278, filed Sep. 18, 2019, US-2020-0095628-A1, Mar. 26, 2020, Allowed.

* cited by examiner

| Reference SNP cluster ID (Rsid) 402 | Chromosome 404 | Position 406 | Alleles 408 |
|---|---|---|---|
| Jan Andriessens' Genome 410 | | | |
| rs4477212 | 1 | 82154 | AA |
| rs4743852 | 9 | 94558126 | TT |
| rs12288326 | 11 | 125123973 | GG |
| rs1902569 | 12 | 125304004 | CT |
| rs838494 | 12 | 125164857 | AA |
| rs5744529 | 5 | 66478392 | CC |
| rs16844308 | 2 | 160619304 | AA |
| ⋮ | ⋮ | ⋮ | ⋮ |
| Linda Andriessens' Genome 412 | | | |
| rs12288326 | 11 | 125123973 | AG |
| rs1902569 | 12 | 125304004 | CT |
| rs838494 | 12 | 125164857 | AA |
| rs5744529 | 5 | 66478392 | CC |
| rs16844308 | 2 | 160619304 | AA |
| i5900414 | 3 | 98304475 | GG |
| rs4743852 | 9 | 94558126 | TT |
| ⋮ | ⋮ | ⋮ | ⋮ |

FIG. 4

Reference Array 502

| Position | 160619304 | 66478392 | 94558126 | 125123973 | 125164857 | 125304004 |
|---|---|---|---|---|---|---|
| Rsid | rs16844308 | rs5744529 | rs4743852 | rs12288326 | rs838494 | rs1902569 |
| Chromosome | 2 | 5 | 9 | 11 | 12 | 12 |

Ordered by Chromosome and Chromosomal Position

Jan Andriessens' Phased Reference Sequence 504

| A | F | K | P | A | G |
|---|---|---|---|---|---|
| 2 | 5 | 9 | 11 | 12 | 12 |

Linda Andriessens' Phased Reference Sequence 506

| A | F | K | D | A | G |
|---|---|---|---|---|---|
| 2 | 5 | 9 | 11 | 12 | 12 |

FIG. 5

HASH-BASED EFFICIENT COMPARISON OF SEQUENCING RESULTS

PRIORITY APPLICATIONS

This application claims priority to or the benefit of U.S. Provisional Patent Application No. 62/734,840, titled, "HASH-BASED EFFICIENT COMPARISON OF SEQUENCING RESULTS," filed Sep. 21, 2018; U.S. Provisional Patent Application No. 62/734,872, titled, "BIN-SPECIFIC AND HASH-BASED EFFICIENT COMPARISON OF SEQUENCING RESULTS," filed Sep. 21, 2018; and U.S. Provisional Patent Application No. 62/734,895, titled, "ORDINAL POSITION-SPECIFIC AND HASH-BASED EFFICIENT COMPARISON OF SEQUENCING RESULTS," filed Sep. 21, 2018. The provisional applications are hereby incorporated by reference for all purposes.

CROSS-REFERENCE TO OTHER APPLICATIONS

The following materials are incorporated by reference as if fully set forth herein:

U.S. patent application Ser. No. 16/575,277 entitled "BIN-SPECIFIC AND HASH-BASED EFFICIENT COMPARISON OF SEQUENCING RESULTS," filed Sep. 18, 2019; and U.S. patent application Ser. No. 16/575,278 entitled "ORDINAL POSITION-SPECIFIC AND HASH-BASED EFFICIENT COMPARISON OF SEQUENCING RESULTS," filed Sep. 18, 2019.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using hashing to compare sequences.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 2 illustrates a phased encoding scheme with sixteen phased pairings that are used to encode the variant data.

FIG. 3 shows an unphased encoding scheme with ten unphased pairings that can also be used to encode the variant data.

FIG. 4 depicts first and second sequenced files that contain variants occurring at different carriers and at different carrier positions.

FIG. 5 illustrates a reference array for those carrier positions that are shared between the first and second sequenced files. FIG. 5 also illustrates first and second sequences respectively generated from the first and second sequenced files based on the reference array.

DETAILED DESCRIPTION

Figure 1:
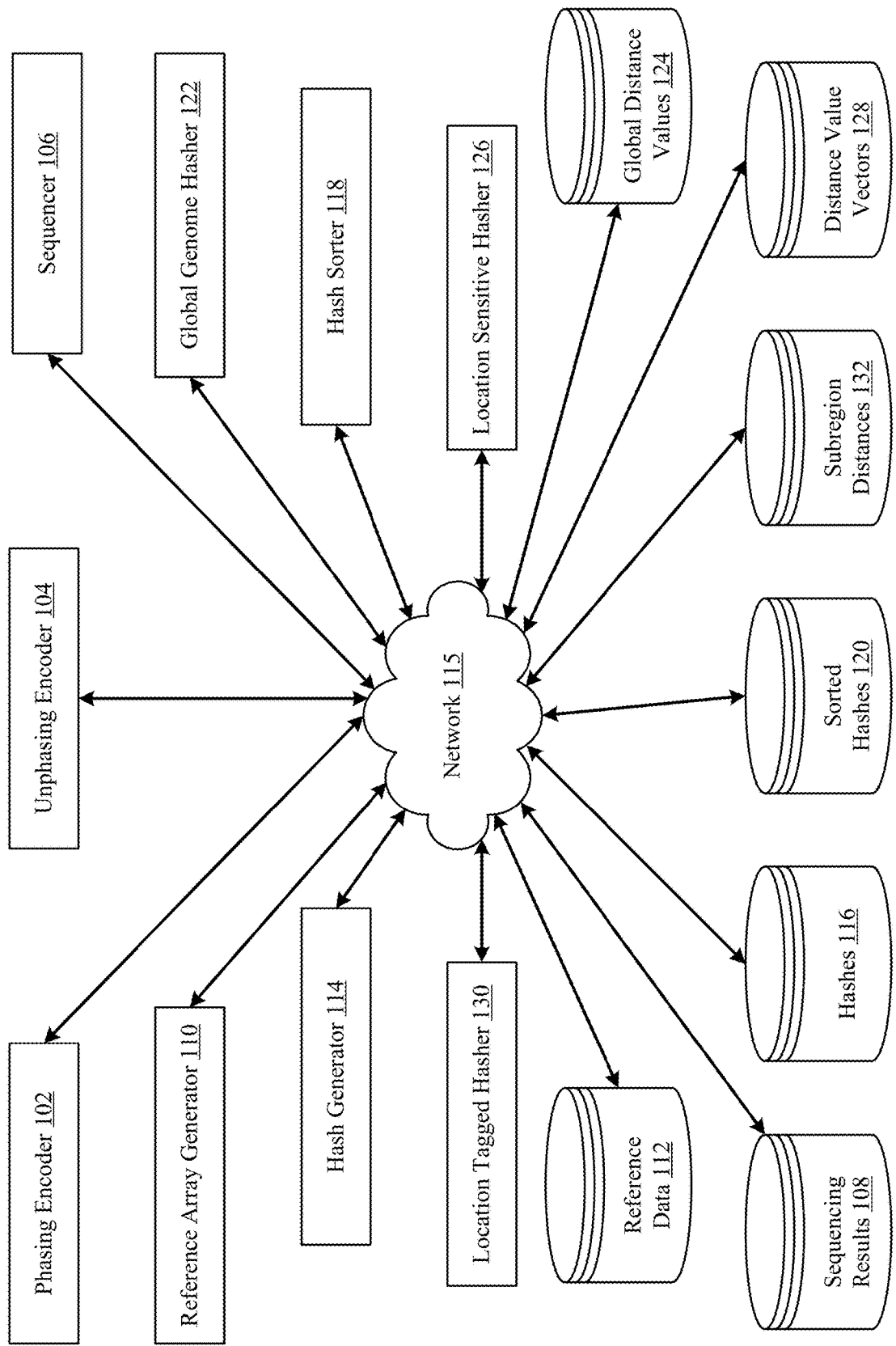
FIG. 1 is a block diagram that shows various aspects of the technology disclosed.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Terminology

A base refers to a nucleotide base or nucleotide, A (adenine), C (cytosine), T (thymine), or G (guanine).

The term "chromosome" refers to the heredity-bearing gene carrier of a living cell, which is derived from chromatin strands comprising DNA and protein components (especially histones). The conventional internationally recognized individual human genome chromosome numbering system is employed herein. This application uses the terms "chromosome" and "carrier" interchangeably.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome. This application uses the terms "site" and "position" interchangeably.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

System

FIG. 1 is a block diagram that shows various aspects of the technology disclosed. We describe a system and various implementations of efficiently comparing sequencing results. The system and processes are described with reference to FIG. 1. Because FIG. 1 is an architectural diagram, certain details are intentionally omitted to improve the clarity of the description.

The system contains the following engines: phasing encoder 102, unphasing encoder 104, sequencer 106, reference array generator 110, hash generator 114, hash sorter 118, global genome hasher 122, location sensitive hasher 126, and location tagged hasher 130.

The system contains the following databases: reference data 112, sequencing results 108, hashes 116, sorted hashes 120, subregion distances 132, distance value vectors 128, and global distance values 124.

In some implementations, the system shown in FIG. 1 can be part of a client, which is deployable to a smartphone or a computer such as a laptop or workstation.

The modules of the system in FIG. 1 can be implemented in hardware or software, and need not be divided up in precisely the same blocks as shown in FIG. 1. Some of the modules can also be implemented on different processors or computers, or spread among a number of different processors or computers. In addition, it will be appreciated that some of the modules can be combined, operated in parallel or in a different sequence than that shown in FIG. 1 without affecting the functions achieved. Also as used herein, the term "module" can include "sub-modules", which themselves can be considered to constitute modules. The blocks in FIG. 1, designated as modules, can also be thought of as flowchart steps in a method. A module also need not necessarily have all its code disposed contiguously in memory; some parts of the code can be separated from other parts of the code with code from other modules or other functions disposed in between.

The interconnections of the elements of the system are now described. The public network(s) 115 couples the engines and the databases, all in communication with each other (indicated by solid double-arrowed lines). The actual communication path can be point-to-point over public and/ or private networks. Some items, such a client, might be delivered indirectly, e.g., via an application store (not shown). The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX. Additionally, a variety of authorization and authentication techniques, such as username/password, Open Authorization (OAuth), Kerberos, SecureID, digital certificates and more, can be used to secure the communications.

Phased and Unphased Encodings

Figure 3:
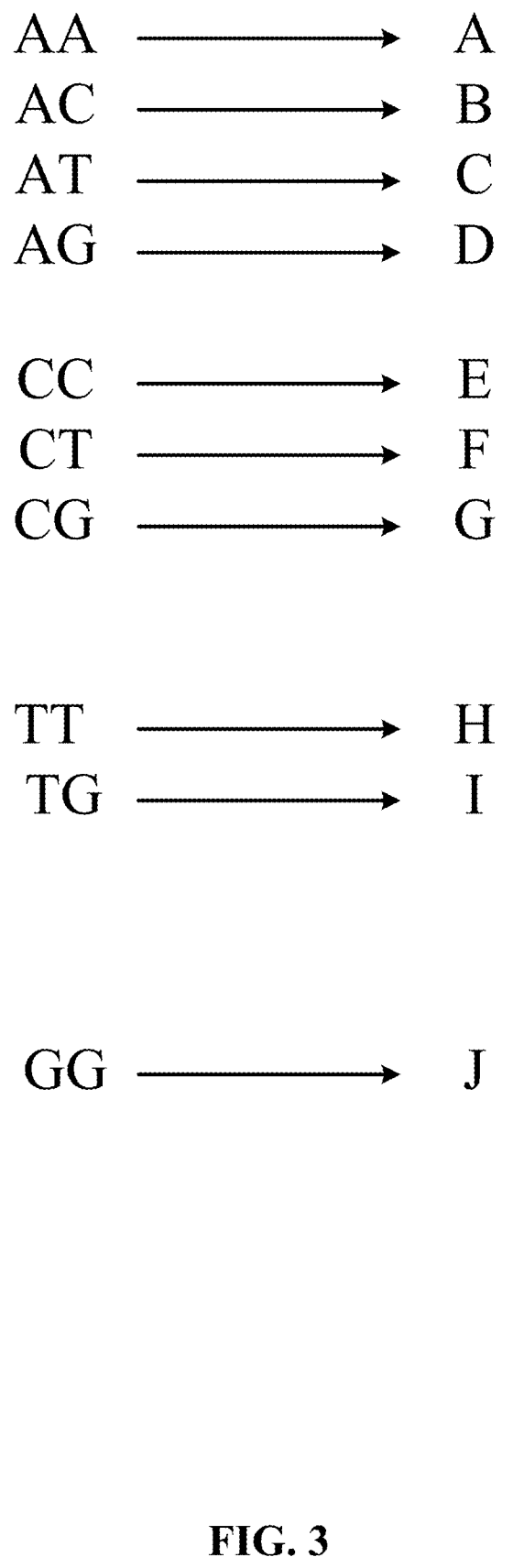

FIG. 2 illustrates a phased encoding scheme with sixteen phased pairings that are used to encode the variant data. The phased encoding is operationalized by the phasing encoder 102. FIG. 3 shows an unphased encoding scheme with ten unphased pairings that can also be used to encode the variant data. The unphased encoding is operationalized by the unphasing encoder 104.

The sixteen phased pairings preserve the ordering of the alleles. For example, phased encoding translates alleles "AC" to "B" and alleles "CA" to "E". In contrast, the ten unphased pairings do not distinguish between "AC" and "CA" and translate them both to "B". The technology disclosed uses the phased encoding to implement phased hashing. In phased hashing, the hashes are generated from phased variant files and can be applied on phased and unphased genomic data. In some implementations, phased location sensitive hashing can be used to quickly phase unphased genomes and impute in subset reference genomes the variants nearby or within the genomic locations contained in the hashes.

Variant Data

FIG. 4 depicts first and second sequenced files that contain variants occurring at different carriers and at different carrier positions. In the illustrated implementation, the first sequenced file or output 410 belongs to a first individual named Jan Andriessens and the second sequenced file or output 412 belongs to a second individual named Linda Andriessens. Each sequenced file can contain variants ranging from ten thousand to three million. The sequenced files can be accessed from genomic sources such as 23&ME™ and Diagnomics™. The variants can be those variants that have highest observed frequency (for example, as determined from minor and/or major allele frequency). The sequenced files can identify the variants by reference SNP cluster ID (Rsid) 402, chromosome 404, chromosome position 406, and base content of the alleles 408. The sequenced files can be generated by the sequencer 106 (e.g., Illumina™ IonTorrent™) and stored in the sequencing results database 108. Once uploaded to a client Reference Array FIG. 5 illustrates a reference array 502 for those carrier positions that are shared or common between the first and second sequenced files 410 and 412. In one implementation, the reference array 502 is generated by the reference array generator 110. In one implementation, the length of the reference array 502 can range from one hundred thousand to one million base positions and can be configured depending on the analysis. In one implementation, the reference array can be ordered by carriers and by carrier positions, as depicted in FIG. 5.

FIG. 5 also illustrates first and second sequences 504 and 506 respectively generated from the first and second sequenced files 410 and 412 based on the reference array 502. The first and second sequences 504 and 506 are independently generated for the two individuals by using the reference array 502 as a template to look up the respective base values that the two individuals have in the first and second sequenced files 410 and 412 at the base positions identified by the reference array 502. As a result, the first and second sequences 504 and 506 have different base values, which are translated by the phased encoding scheme of FIG. 2. Accordingly, the first and second sequences 504 and 506 contain the translated phased encodings ranging from "A" to "P", as shown in FIG. 2. In one implementation, the first and second sequences 504 and 506 are stored in the reference database 112.

Hash Generation

A DNA hash is a subset of DNA patterns with a fixed or variable length that occur in a genome. These can be used to match with another DNA hash from another genome. Patterns typically occur only a few times in the genome. A distance value can be determined by calculating the percentage of matching patterns between two hashes. The length of the patterns and the maximum (and minimum) hits in a genome can vary based on the desired application.

Hashes can be generated on reference genomes and subsets of them. In general, they are the intersection of available positions on one or multiple genomes, ordered by chromosome and chromosomal position. Flexible reference genome are key to a broad range of genomic queries. For example, a subset of genomic positions related to a trait can form a new reference genome to address that specific trait.

Figure 6:
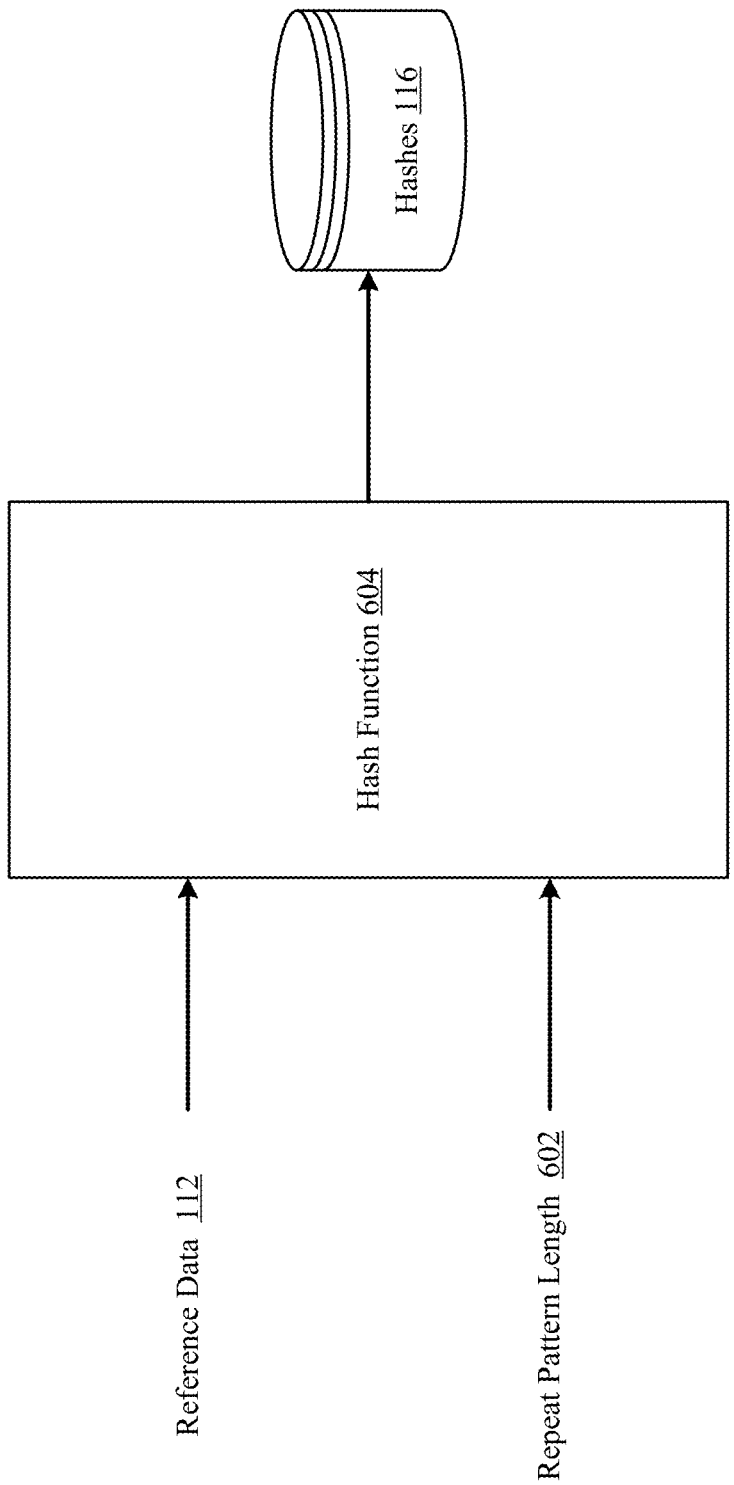
FIG. 6 shows how hashes are generated over a selected pattern length of positions in the reference array to independently produce non-unique window hashes for base patterns in the first and second sequences.
Figure 7:
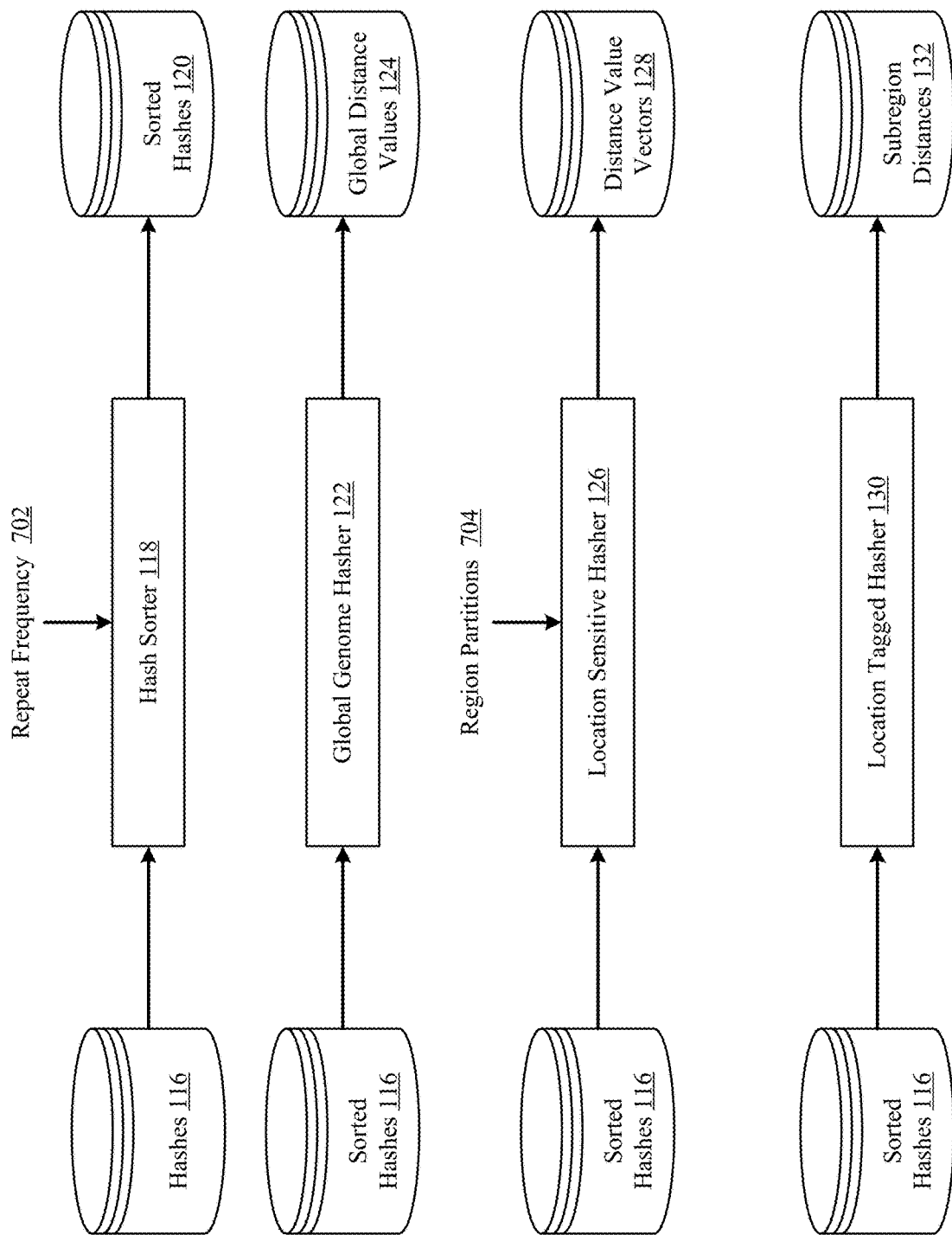
FIG. 7 depicts various hashing implementations of the technology disclosed, including global genome hashing, location sensitive hashing, and location tagged hashing.

FIG. 6 shows how hashes are generated over a selected pattern length 602 of positions in the reference array 502 to independently produce non-unique window hashes for base patterns in the first and second sequences 504 and 506. The hashes are generated by the hash function 604, which is a cryptographic algorithm such as SHA-1, SHA-2, SHA-256, and SHA-384. The hash function 604 is applied to the translated phased encodings in the first and second sequences 504 and 506 (stored in the reference database 112). In one implementation, the selected pattern length 602 of positions can range from fifteen to forty bases. In some implementations, the selected pattern length 602 of positions is selected based on the length of the reference array 502. In other implementations, the pattern length 602 is selected based on the analysis being conducted. The window hashes are separately and independently generated over the pattern length 602 for patterns in the first and second sequences 504 and 506 and are stored in the hashes database 116.

Hash Sorting

Once the window hashes are generated for the first and second sequences 504 and 506, they are stored based on their repeat or occurrence frequency 702. That is, only those hash windows are selected that occur less than a ceiling number of times. In one implementation, the ceiling number of times ranges from one to ten and can be configured depending on the analysis. The hash sorting is performed by the hash sorter 118 and stored in the sorted hashes database 120.

For the first and second sequences 504 and 506, once those window hashes are identified that respectively occur less than a ceiling number of times, then they can be compared between the first and second sequences 504 and 506 using a variety of analysis-specific techniques, including global genome hashing, location sensitive hashing, and location tagged hashing.

Global Genome Hashing

Global genome hashing generates a global hash across the genome. Global genome hashing is implemented by the global genome hasher 122, which operates on the sorted hashes 116. When two hashes are compared, a global distance value is calculated and stored in the global distance values database 124. The global genome hasher 122 accesses the window hashes that occur less than a ceiling number of times and compares the selected window hashes to identify common window hashes between the first and second sequences. The global genome hasher 122 then determines a similarity measure between the first and second sequences based on the common window hashes. In one implementation, the similarity measure is determined by a distance formula defined as $$1 - \frac{\text{number of common window hashes}}{\text{number of unique window hashes}}.$$

Global genome hashing is used by the technology disclosed for fast DNA comparison without privacy loss. Global genome hashing provides a fast, anonymous, and robust way of calculating distances between genomes. The hash is only a fraction (10-1000kb) of the total genome, but still allows to calculate distances between genomes in a couple of milliseconds. Some example applications of global genome hashing include genetic distance trees (FIG. 8), online and wireless mobile DNA search engines, and genealogy databases.

Location Sensitive Hashing

Location sensitive hashing generates a global hash matrix with individual hashes within defined partitions on the reference genome. When two location sensitive hashing matrices are compared, a distance value vector is calculated that allows region specific comparisons between genomes. Location sensitive hashing is implemented by the location sensitive hasher 126, which also operates on the sorted hashes 116. The distance value vector is stored in the distance value vectors database 128.

The location sensitive hasher 126 accesses the window hashes that occur less than a ceiling number of times and compares the selected window hashes between the first and second sequences on a bin-by-bin basis such that a first set of selected window hashes produced for base patterns in a given bin in the first sequenced output are compared only to a second a set of selected window hashes produced for base patterns in the given bin in the second sequenced output. The location sensitive hasher 126 can then identify common window hashes for each bin in the first and second sequences based on the comparing and further determine a similarity measure for each bin based on the common window hashes. The location sensitive hasher 126 can also require that the selected window hashes in the first set completely match with the corresponding selected window hashes in the second set. The bins are defined for the first and second sequenced outputs on a carrier-by-carrier basis by region partitions 704. Each bin can contain five hundred to thousand variants. In other implementations, each bin can span across one hundred thousand to one million bases. In yet other implementations, each bin can span across multiple units (genes).

Location Tagged Hashing

Location tagged hashing generates a matrix of hashes with an exact genomic location within the reference genome. When two location tagged hashing matrices are compared, distances for subregions can be measured by looking for hash matches on the genomic locations within the region. Location tagged hashing is implemented by the location tagged hasher 130, which also operates on the sorted hashes 116. The subregion distance is stored in the subregion distances database 132. The location tagged hasher 130 accesses the window hashes that occur less than a ceiling number of times and compares the selected window hashes between the first and second sequences on a starting position basis such that selected window hashes for base patterns having same start positions in the read results are compared. In implementations, the starting positions can be chromosomal positions or sites. The location sensitive hasher 126 can then identify common window hashes between the first and second sequences based on the comparing and further determine a similarity measure between the first and second sequences based on the common window hashes.

In one implementation, for the bin-wise similarity measures, the system can require that the selected window hashes between the corresponding bins substantially match. The substantial matching can be determined by a threshold number of hits between the corresponding bins. The threshold is a hyperparameter that can be configured for different analysis. In one implementation, the threshold used for identifying ethnic ancestry or ethnic origins is lower than that used for determining inherited traits.

Based on the bin-wise and/or starting position-wise similarity measures, the technology disclosed determines a percentage of shared bases between the sequencing results. In some implementations, the percentage of shared bases can be determined on a carrier-by-carrier basis.

Distance Tree Visualization

Figure 8:
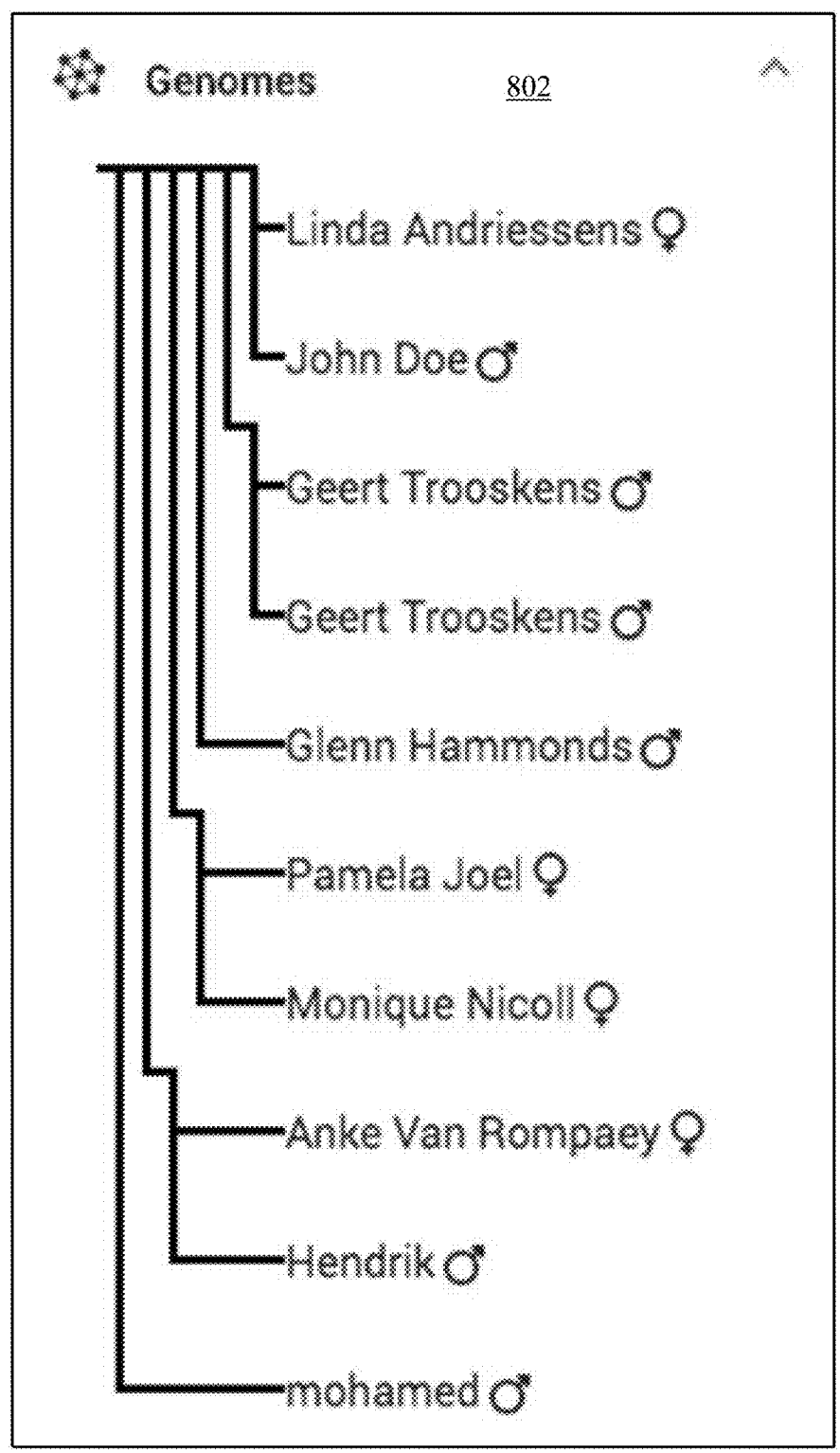
FIG. 8 is one implementation of a distance tree visualization.

FIG. 8 is one implementation of a distance tree visualization 802. In some implementations, the technology disclosed can use the percentage of shared bases to identify common ancestors and close and distant relatives. In one implementation, the distance tree visualization 802 can be generated based on the percentage of shared bases to identify the degree of relatedness between individuals.

Bin-Wise Genome Comparison

Figure 9:
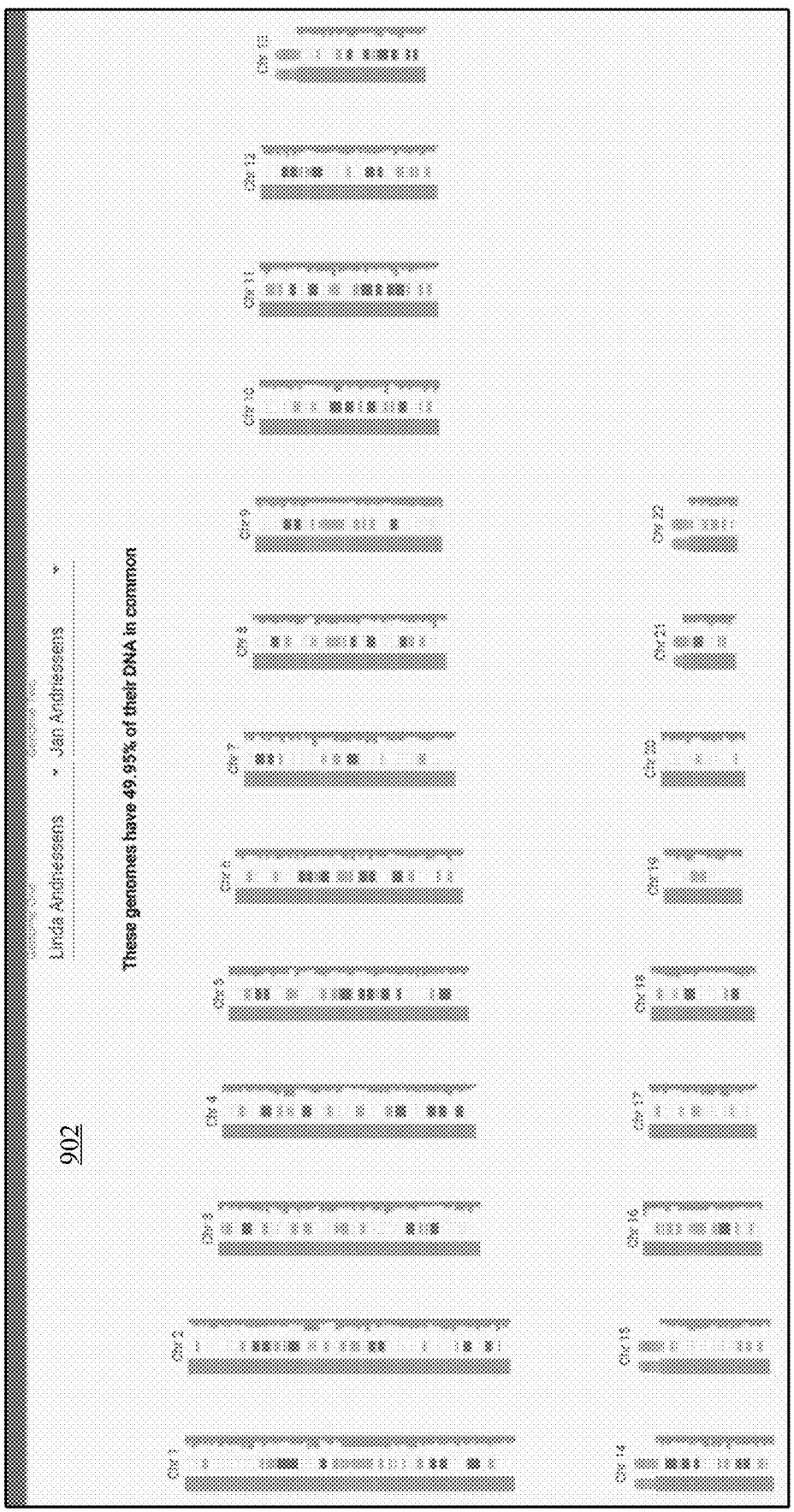
FIG. 9 shows an example bin-wise comparison between genomes of two individuals as implemented by the location sensitive hashing.

FIG. 9 shows an example bin-wise comparison 902 between genomes of two individuals as implemented by the location sensitive hashing. In some implementations, the technology disclosed can use the percentage of shared bases to determine traits inherited from an ancestor. For example, if a particular chromosome, a particular gene, or a particular part of the gene is known to be associated with a disease and an ancestor of an individual had that disease, then the percentage of shared bases can identify whether the individual inherited the pathogenic bases from the ancestor and thus is susceptible to the disease.

Ethnic Origination Discovery

Figure 10:
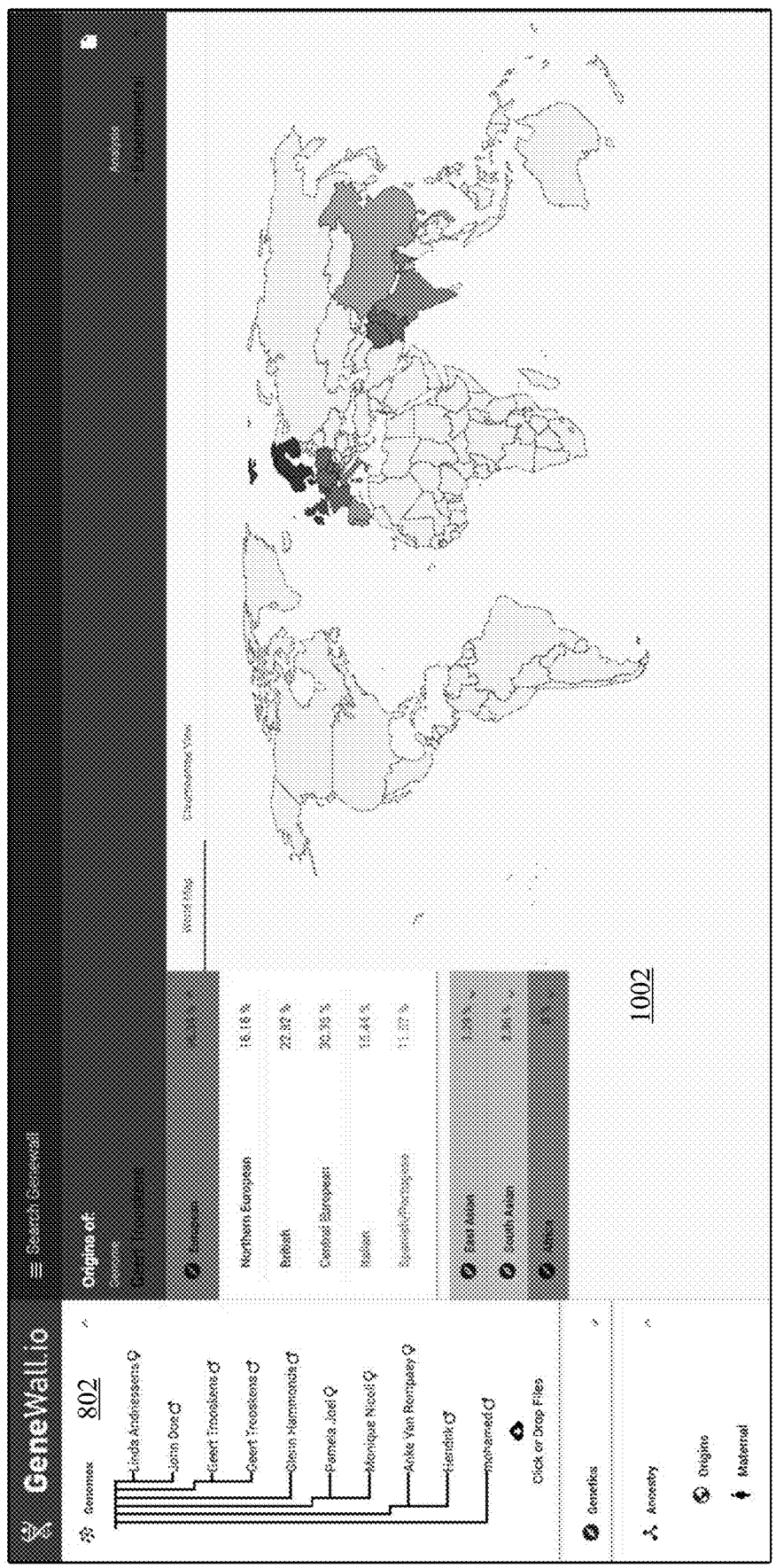
FIG. 10 illustrates one implementation of determining ethnic ancestry or ethnic origins of an individual using the location sensitive hashing and/or the location tagged hashing.

FIG. 10 illustrates one implementation of determining ethnic ancestry or ethnic origins 1002 of an individual using the location sensitive hashing and/or the location tagged hashing. Based on the percentage of shared bases, the system can identify ethnic ancestry or ethnic origins of the given individual across multiple ethnicities and sub-ethnicities. For example, known template read results representing ethnicities like European, Asian, and African and sub-ethnicities like Norther European, British, Central European, Italian, Spanish/Portugese, East Asian, and South Asian can be compared against the given individual's read results to determine what percentage of the given individual's genome originates from different ethnic and sub-ethnic groups.

Genome Browser

Figure 11A:
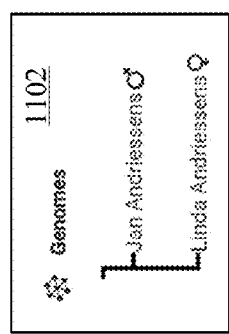
FIGS. 11A, 11B, and 11C show one implementation of a genomic browser that presents comparative visualizations of genomic content of two individuals.
Figure 11A:
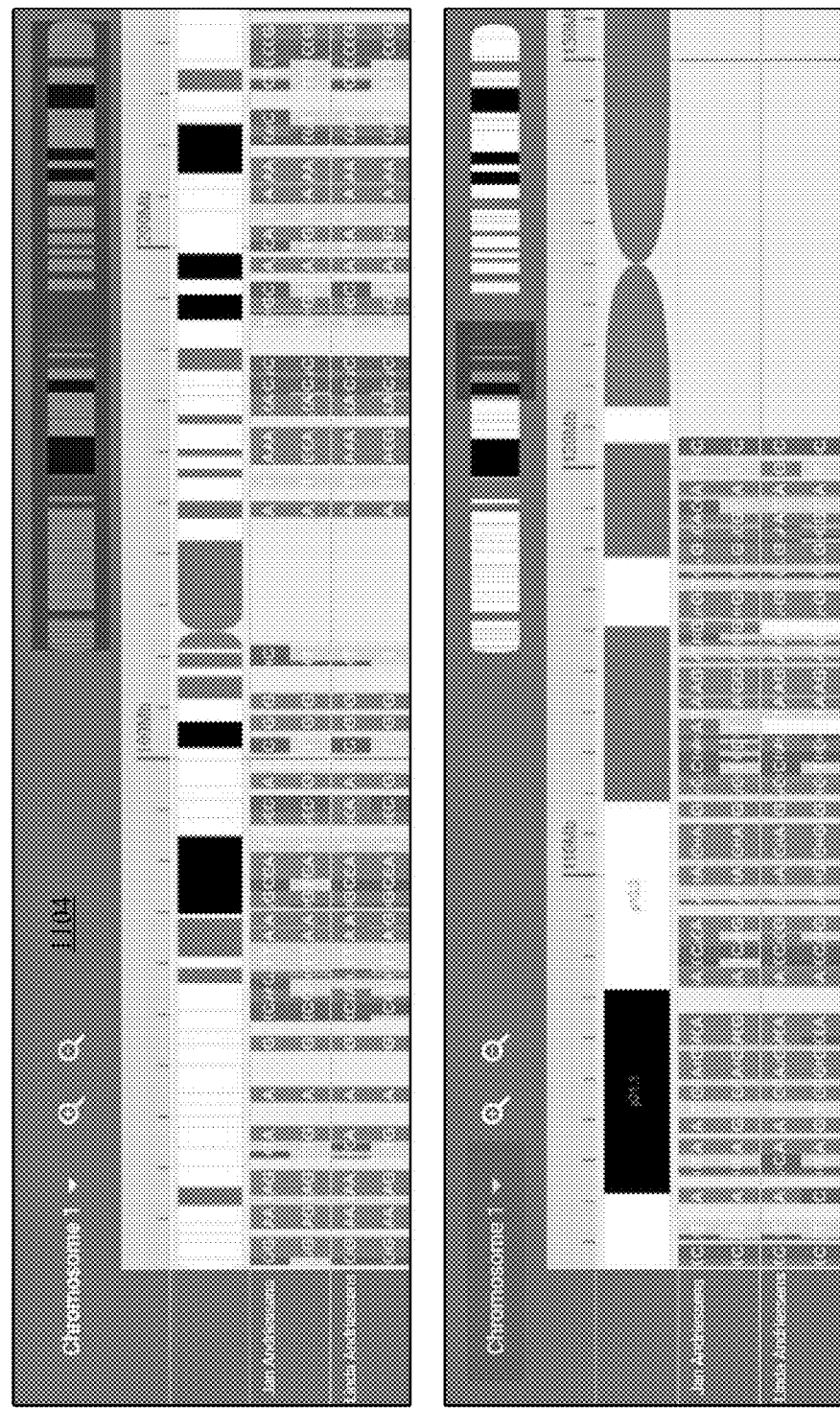
Figure 11B:
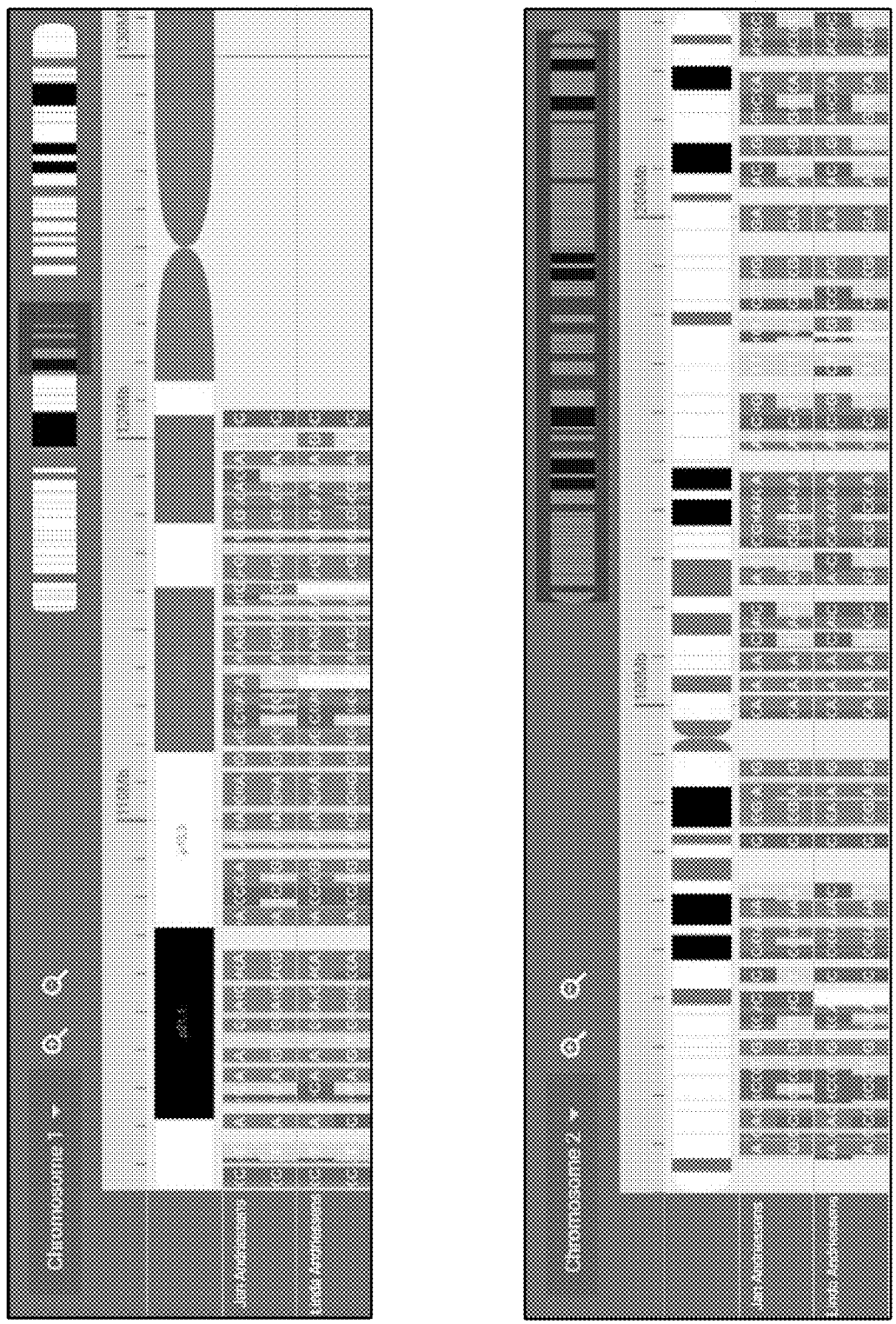
Figure 11C:

FIGS. 11A, 11B, and 11C show one implementation of a genomic browser 1104 that presents comparative visualizations of genomic content of two individuals 1102. The genomic browser 1104 visualizes base content of the various chromosomes 1112 of the two individuals 1102, with zoom-in and zoom-out options that change the size of the based content being analyzed and compared between the two individuals 1102.

Computer System

Figure 12:
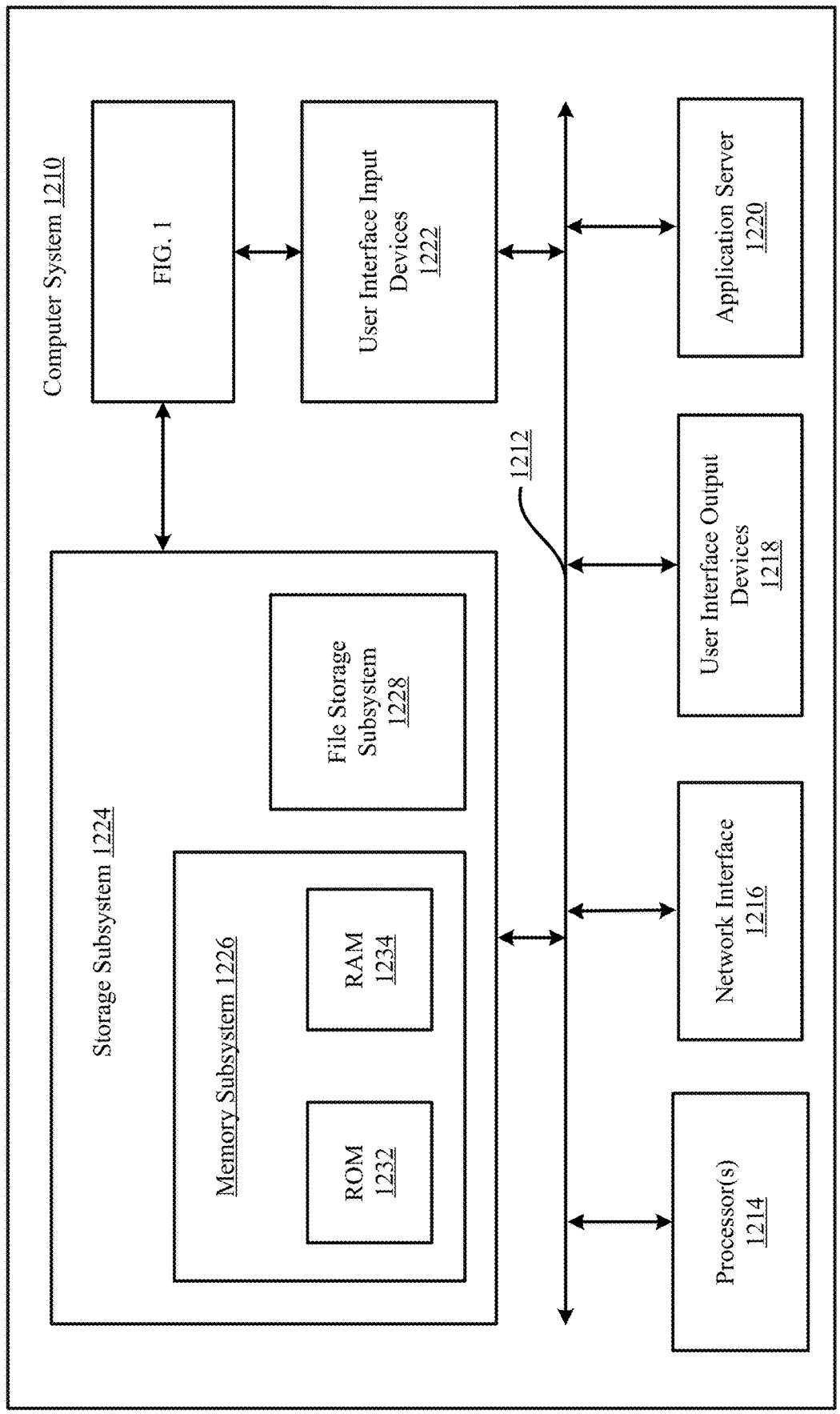
FIG. 12 is a simplified block diagram of a computer system that can be used to implement the technology disclosed.

FIG. 12 is a simplified block diagram of a computer system that can be used to implement the technology disclosed. Computer system 1210 typically includes one or more processors 1214 that communicate with a number of peripheral devices via bus subsystem 1212. These peripheral devices can include a storage subsystem 1224 including, for example, a memory subsystem 1226 and a file storage subsystem 1228, user interface input devices 1222, user interface output devices 1218, and a network interface 1216. The input and output devices allow user interaction with the computer system 1210. The network interface 1216 provides an interface to outside networks, including an interface to corresponding interface devices in other computer systems.

In one implementation, one or more components of FIG. 1 are communicably linked to the storage subsystem 1224 and the user interface input devices 1222.

The user interface input devices 1222 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into the computer system 1210.

The user interface output devices 1218 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from the computer system 1210 to the user or to another machine or computer system.

The storage subsystem 1224 stores programming and data constructs that provide the functionality of some or all of the modules and methods described herein. These software modules are generally executed by the processors 1214 alone or in combination with other processors.

The memory subsystem 1226 used in the storage subsystem 1224 can include a number of memories including a main random access memory (RAM) 1234 for storage of instructions and data during program execution and a read only memory (ROM) 1232 in which fixed instructions are stored. The file storage subsystem 1228 can provide persistent storage for program and data files, and can include a hard disk drive, a floppy disk drive along with associated removable media, a CD-ROM drive, an optical drive, or removable media cartridges. The modules implementing the functionality of certain implementations can be stored by the file storage subsystem 1228 in the storage subsystem 1224, or in other machines accessible by the processors 1214.

The bus subsystem 1212 provides a mechanism for letting the various components and subsystems of the computer system 1210 communicate with each other as intended. Although the bus subsystem 1212 is shown schematically as a single bus, alternative implementations of the bus subsystem 1212 can use multiple busses.

Application server 1220 can be a framework that allows the applications of the computer system 1210 to run, such as the hardware and/or software, e.g., the operating system.

The computer system 1210 can be of varying types including a workstation, server, computing cluster, blade server, server farm, or any other data processing system or computing device. Due to the ever-changing nature of computers and networks, the description of the computer system 1210 depicted in FIG. 12 is intended only as one example. Many other configurations of the computer system 1210 are possible having more or fewer components than the computer system depicted in FIG. 12.

Any data structures and code described or referenced above are stored according to many implementations on a computer-readable storage medium, which may be any device or medium that can store code and/or data for use by a computer system. This includes, but is not limited to, volatile memory, non-volatile memory, application-specific integrated circuits (ASICs), field-programmable gate arrays (FPGAs), magnetic and optical storage devices such as disk drives, magnetic tape, CDs (compact discs), DVDs (digital versatile discs or digital video discs), or other media capable of storing computer-readable media now known or later developed.

Some Particular Implementations

We describe a system and various implementations of efficiently comparing sequencing results. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections— these recitations are hereby incorporated forward by reference into each of the following implementations.

In one implementation, the technology disclosed presents a system. The system runs on one or more processors coupled to memory. The memory is loaded with computer instructions to efficiently compare read results. The instructions, when executed on the processors, implement the following actions.

First, the system generates a reference array of variant data for locations that are shared between read results which are to be compared. In one implementation, the length of the reference array can range from one hundred thousand to one million base positions. In one implementation, the reference array can be ordered by carriers and by carrier positions, as depicted in FIG. 5.

The system then generates hashes over a selected pattern length of positions in the reference array to independently produce non-unique window hashes for base patterns in the read results. In one implementation, the selected pattern length of positions can range from fifteen to forty bases.

The system then selects for comparison window hashes that occur less than a ceiling number of times. In one implementation, the ceiling number of times ranges from one to ten.

The system then compares the selected window hashes to identify common window hashes between the read results.

The system then determines a similarity measure for the read results based on the common window hashes. In one implementation, the similarity measure can be determined by a distance formula defined as $$1 - \frac{\text{number of common window hashes}}{\text{number of unique window hashes}}.$$

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The variant data can contain those variants that have highest observed frequency (for example, as determined from minor and/or major allele frequency). In one implementation, the variant data can be identified by sixteen phased pairings, as depicted in FIG. 2. In other implementations, the variant data can be identified by ten unphased pairings, as depicted in FIG. 3.

In one implementation, the pattern length of positions can be selected based on the length of the reference array.

In some implementations, the read results can be partitioned into bins. In such implementations, the system compares the selected window hashes between the read results on a bin-by-bin basis such that selected window hashes for base patterns occurring in corresponding bins in the read results are compared. Then, based on the comparing, the system identifies common window hashes between the corresponding bins. Further, the system determines a similarity measure for the corresponding bins based on the common window hashes.

In one implementation, the system requires that the selected window hashes between the corresponding bins completely match. Based on the bin-wise similarity measures, the system determines a percentage of shared bases between the read results. In some implementations, the percentage of shared bases can be determined on a carrier-by-carrier basis.

In some implementations, the system can use the percentage of shared bases to determine traits inherited from an ancestor. For example, if a particular chromosome, a particular gene, or a particular part of the gene is known to be associated with a disease and an ancestor of an individual had that disease, then the percentage of shared bases can identify whether the individual inherited the pathogenic bases from the ancestor and thus is susceptible to the disease.

In some implementations, the system can use the percentage of shared bases to identify common ancestors and close and distant relatives. In one implementation, a distance tree visualization can be generated based on the percentage of shared bases to identify the degree of relatedness between individuals.

In some implementations, based on the bin-wise similarity measures, the system can determine a percentage of shared bases between a given individual's read results and ethnicity-specific read results. Based on the percentage of shared bases, the system can identify ethnic ancestry or ethnic origins of the given individual across multiple ethnicities and sub-ethnicities. For example, known template read results representing ethnicities like European, Asian, and African and sub-ethnicities like Norther European, British, Central European, Italian, Spanish/Portugese, East Asian, and South Asian can be compared against the given individual's read results to determine what percentage of the given individual's genome originates from different ethnic and sub-ethnic groups.

In one implementation, for the bin-wise similarity measures, the system can require that the selected window hashes between the corresponding bins substantially match. The substantial matching can be determined by a threshold number of hits between the corresponding bins. The threshold is a hyperparameter that can be configured for different analysis. In one implementation, the threshold used for identifying ethnic ancestry or ethnic origins is lower than that used for determining inherited traits.

The bins can be defined for the read results on a carrier-by-carrier basis. In one implementation, each bin can contain five hundred to thousand variants. In another implementation, each bin can span across one hundred thousand to one million bases. In yet another implementation, each bin can span across multiple units.

In some implementations, the system compares the selected window hashes between the read results on a starting position basis such that selected window hashes for base patterns having same start positions in the read results are compared. Based on the comparison, the system identifies common window hashes between the read results. The system then determines a similarity measure between the read results based on the common window hashes.

In one implementation, the system determines a percentage of shared bases between the read results based on the starting position-wise similarity measures. In some implementations, the percentage of shared bases can be determined on a carrier-by-carrier basis.

In one implementation, the system determines inherited traits based on the percentage of shared bases as determined from the starting position-wise similarity measures. In another implementation, the system identifies common ancestors and close and distant relatives based on the percentage of shared bases as determined from the starting position-wise similarity measures. In yet another implementation, based on the starting position-wise similarity measures, the system determines a percentage of shared bases between a given individual's read results and ethnicity-specific read results and identifies ethnic ancestry or ethnic origins of the given individual based on the percentage of shared bases. In yet further implementations, based on the starting position-wise similarity measures, the system generates a distance tree visualization between the read results.

Other implementations may include a non-transitory computer readable storage medium storing instructions executable by a processor to perform actions of the system described above. Each of the features discussed in the particular implementation section for other implementations apply equally to this implementation. As indicated above, all the other features are not repeated here and should be considered repeated by reference.

In one implementation, the technology disclosed presents a computer-implemented method of efficiently comparing read results.

The method includes generating a reference array of variant data for locations shared between read results to be compared.

The method includes generating hashes over a selected pattern length of positions in the reference array to independently produce non-unique window hashes for base patterns in the read results.

The method includes selecting for comparison window hashes that occur less than a ceiling number of times.

The method includes comparing the selected window hashes to identify common window hashes between the read results.

The method includes determining a similarity measure for the read results based on the common window hashes.

Other implementations may include a non-transitory computer readable storage medium (CRM) storing instructions executable by a processor to perform the computer-implemented method described above. Yet another implementation may include a system including memory and one or more processors operable to execute instructions, stored in the memory, to perform the computer-implemented method described above. Each of the features discussed in the particular implementation section for other implementations apply equally to this implementation. As indicated above, all the other features are not repeated here and should be considered repeated by reference.

In another implementation, the technology disclosed presents a system. The system runs on one or more processors coupled to memory. The memory is loaded with computer instructions to efficiently compare sequenced files. The instructions, when executed on the processors, implement the following actions.

First, the system accesses a first sequenced file and a second sequenced file. The first sequenced file can belong to a first individual and the second sequenced file can belong to a second individual. The first and second sequenced files contain variants occurring at different carriers and at different carrier positions, as depicted in FIG. 4. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The system then generates a reference array for those carrier positions that are shared between the first and second sequenced files, as shown in FIG. 5. In one implementation, the length of the reference array can range from one hundred thousand to one million base positions. In one implementation, the reference array can be ordered by carriers and by carrier positions, as depicted in FIG. 5.

The system then, based on the reference array, generates a first sequence from the first sequenced file and a second sequence from the second sequenced file, as shown in FIG. 5.

The system then generates hashes over a selected pattern length of positions in the reference array to independently produce non-unique window hashes for base patterns in the first and second sequences. In one implementation, the selected pattern length of positions can range from fifteen to forty bases.

The system then selects for comparison window hashes that occur less than a ceiling number of times.

The system then compares the selected window hashes to identify common window hashes between the first and second sequences.

The system then determines a similarity measure between the first and second sequences based on the common window hashes. In one implementation, the similarity measure can be determined by a distance formula defined as $$\frac{1 - \text{number of common window hashes}}{\text{number of unique window hashes}}.$$

In some implementations, based on the similarity measure, the system generates a distance tree between the first and second sequences.

Each of the features discussed in the particular implementation section for other implementations apply equally to this implementation. As indicated above, all the other features are not repeated here and should be considered repeated by reference.

In one implementation, the technology disclosed presents a computer-implemented method of efficiently comparing sequenced files.

The method includes accessing a first sequenced file and a second sequenced file. The first sequenced file can belong to a first individual and the second sequenced file can belong to a second individual. The first and second sequenced files contain variants occurring at different carriers and at different carrier positions, as depicted in FIG. 4. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The method includes generating a reference array for those carrier positions that are shared between the first and second sequenced files, as shown in FIG. 5. In one implementation, the length of the reference array can range from one hundred thousand to one million base positions. In one implementation, the reference array can be ordered by carriers and by carrier positions, as depicted in FIG. 5.

The method includes, based on the reference array, generating a first sequence from the first sequenced file and a second sequence from the second sequenced file, as shown in FIG. 5.

The method includes generating hashes over a selected pattern length of positions in the reference array to independently produce non-unique window hashes for base patterns in the first and second sequences.

The method includes selecting for comparison window hashes that occur less than a ceiling number of times.

The method includes comparing the selected window hashes to identify common window hashes between the first and second sequences.

The method includes determining a similarity measure between the first and second sequences based on the common window hashes. In one implementation, the similarity measure can be determined by a distance formula defined as $$\frac{1 - \text{number of common window hashes}}{\text{number of unique window hashes}}.$$

Other implementations may include a non-transitory computer readable storage medium (CRM) storing instructions executable by a processor to perform the computer-implemented method described above. Yet another implementation may include a system including memory and one or more processors operable to execute instructions, stored in the memory, to perform the computer-implemented method described above. Each of the features discussed in the particular implementation section for other implementations apply equally to this implementation. As indicated above, all the other features are not repeated here and should be considered repeated by reference.

In one implementation, the technology disclosed presents a system. The system runs on one or more processors coupled to memory. The memory is loaded with computer instructions to efficiently compare sequenced outputs. The instructions, when executed on the processors, implement the following actions.

First, the system accesses a first sequenced output and a second sequenced output. The first sequenced output can belong to a first individual and the second sequenced output can belong to a second individual. The first and second sequenced outputs contain variants occurring at different carriers and at different carrier positions, as depicted in FIG. 4. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The system then generates a reference array for those carrier positions that are shared between the first and second sequenced outputs, as shown in FIG. 5. In one implementation, the length of the reference array can range from one hundred thousand to one million base positions. In one implementation, the reference array can be ordered by carriers and by carrier positions, as depicted in FIG. 5.

The system then, based on the reference array, generates a first sequence from the first sequenced output and a second sequence from the second sequenced output, as shown in FIG. 5.

The system then generates hashes over a selected pattern length of positions in the reference array to independently produce non-unique window hashes for base patterns in the first and second sequences. In one implementation, the selected pattern length of positions can range from fifteen to forty bases.

The system then selects for comparison window hashes that occur less than a ceiling number of times.

The system then compares the selected window hashes between the first and second sequences on a starting position basis such that selected window hashes for base patterns having same start positions in the read results are compared. In some implementations, the system compares the selected window hashes between the first and second sequences on the starting position basis such that a first selected window hash produced for a base pattern having a given start position in the first sequence is compared only to a second selected window hash produced for a base pattern having the given start position in the second sequence.

The system then identifies common window hashes between the first and second sequences based on the comparing.

The system then determines a similarity measure between the first and second sequences based on the common window hashes. In one implementation, the similarity measure can be determined by a distance formula defined as $$1 - \frac{\text{number of common window hashes}}{\text{number of unique window hashes}}.$$

In some implementations, based on the similarity measure, the system generates a distance tree between the first and second sequences.

Each of the features discussed in the particular implementation section for other implementations apply equally to this implementation. As indicated above, all the other features are not repeated here and should be considered repeated by reference.

In one implementation, the technology disclosed presents a computer-implemented method of efficiently comparing sequenced outputs.

The method includes accessing a first sequenced output and a second sequenced output. The first sequenced output can belong to a first individual and the second sequenced output can belong to a second individual. The first and second sequenced outputs contain variants occurring at different carriers and at different carrier positions, as depicted in FIG. 4. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The method includes generating a reference array for those carrier positions that are shared between the first and second sequenced outputs, as shown in FIG. 5. In one implementation, the length of the reference array can range from one hundred thousand to one million base positions. In one implementation, the reference array can be ordered by carriers and by carrier positions, as depicted in FIG. 5.

The method includes, based on the reference array, generating a first sequence from the first sequenced output and a second sequence from the second sequenced output, as shown in FIG. 5.

The method includes generating hashes over a selected pattern length of positions in the reference array to independently produce non-unique window hashes for base patterns in the first and second sequences.

The method includes selecting for comparison window hashes that occur less than a ceiling number of times.

The method includes comparing the selected window hashes between the first and second sequences on a starting position basis such that selected window hashes for base patterns having same start positions in the read results are compared. In some implementations, the method includes comparing the selected window hashes between the first and second sequences on the starting position basis such that a first selected window hash produced for a base pattern having a given start position in the first sequence is compared only to a second selected window hash produced for a base pattern having the given start position in the second sequence.

The method includes identifying common window hashes between the first and second sequences based on the comparing.

The method includes determining a similarity measure between the first and second sequences based on the common window hashes. In one implementation, the similarity measure can be determined by a distance formula defined as $$\frac{1 - \text{number of common window hashes}}{\text{number of unique window hashes}}.$$

Other implementations may include a non-transitory computer readable storage medium (CRM) storing instructions executable by a processor to perform the computer-implemented method described above. Yet another implementation may include a system including memory and one or more processors operable to execute instructions, stored in the memory, to perform the computer-implemented method described above. Each of the features discussed in the particular implementation section for other implementations apply equally to this implementation. As indicated above, all the other features are not repeated here and should be considered repeated by reference.

In one implementation, the technology disclosed presents a system. The system runs on one or more processors coupled to memory. The memory is loaded with computer instructions to efficiently compare sequenced outputs. The instructions, when executed on the processors, implement the following actions.

First, the system accesses a first sequenced output and a second sequenced output. The first sequenced output can belong to a first individual and the second sequenced output can belong to a second individual. The first and second sequenced outputs contain variants occurring at different carriers and at different carrier positions and are partitioned into bins. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The system then generates a reference array for those carrier positions that are shared between the first and second sequenced outputs, as shown in FIG. 5. In one implementation, the length of the reference array can range from one hundred thousand to one million base positions. In one implementation, the reference array can be ordered by carriers and by carrier positions, as depicted in FIG. 5.

The system then, based on the reference array, generates a first sequence from the first sequenced output and a second sequence from the second sequenced output, as shown in FIG. 5.

The system then generates hashes over a selected pattern length of positions in the reference array to independently produce non-unique window hashes for base patterns in the first and second sequences. In one implementation, the selected pattern length of positions can range from fifteen to forty bases.

The system then selects for comparison window hashes that occur less than a ceiling number of times.

The system then compares the selected window hashes between the first and second sequences on a bin-by-bin basis such that a first set of selected window hashes produced for base patterns in a given bin in the first sequenced output are compared only to a second a set of selected window hashes produced for base patterns in the given bin in the second sequenced output. In some implementations, the system requires that the selected window hashes in the first set completely match with the corresponding selected window hashes in the second set.

The system then identifies common window hashes for each bin in the first and second sequences based on the comparing.

The system then determines a similarity measure for each bin based on the common window hashes. In one implementation, the similarity measure can be determined by a distance formula defined as $$\frac{1 - \text{number of common window hashes}}{\text{number of unique window hashes}}.$$

In some implementations, based on the similarity measure, the system generates a distance tree between the first and second sequences.

Each of the features discussed in the particular implementation section for other implementations apply equally to this implementation. As indicated above, all the other features are not repeated here and should be considered repeated by reference.

In one implementation, the technology disclosed presents a computer-implemented method of efficiently comparing sequenced outputs.

The method includes accessing a first sequenced output and a second sequenced output. The first sequenced output can belong to a first individual and the second sequenced output can belong to a second individual. The first and second sequenced outputs contain variants occurring at different carriers and at different carrier positions and are partitioned into bins. The variants can be those variants that have highest observed frequency (for example, as determined from minor and/or major allele frequency). In one implementation, the variants are identified by sixteen phased pairings, as depicted in FIG. 2. In other implementations, the variants are identified by ten unphased pairings, as depicted in FIG. 3.

The method includes generating a reference array for those carrier positions that are shared between the first and second sequenced outputs, as shown in FIG. 5. In one implementation, the length of the reference array can range from one hundred thousand to one million base positions. In one implementation, the reference array can be ordered by carriers and by carrier positions, as depicted in FIG. 5.

The method includes, based on the reference array, generating a first sequence from the first sequenced output and a second sequence from the second sequenced output, as shown in FIG. 5.

The method includes generating hashes over a selected pattern length of positions in the reference array to independently produce non-unique window hashes for base patterns in the first and second sequences.

The method includes selecting for comparison window hashes that occur less than a ceiling number of times.

The method includes comparing the selected window hashes between the first and second sequences on a bin-by-bin basis such that a first set of selected window hashes produced for base patterns in a given bin in the first sequenced output are compared only to a second a set of selected window hashes produced for base patterns in the given bin in the second sequenced output.

The method includes identifying common window hashes for each bin in the first and second sequences based on the comparing.

The method includes determining a similarity measure for each bin based on the common window hashes. In one implementation, the similarity measure can be determined by a distance formula defined as $$1 - \frac{\text{number of common window hashes}}{\text{number of unique window hashes}}.$$

Other implementations may include a non-transitory computer readable storage medium (CRM) storing instructions executable by a processor to perform the computer-implemented method described above. Yet another implementation may include a system including memory and one or more processors operable to execute instructions, stored in the memory, to perform the computer-implemented method described above. Each of the features discussed in the particular implementation section for other implementations apply equally to this implementation. As indicated above, all the other features are not repeated here and should be considered repeated by reference.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A computer-implemented method of efficiently comparing read results, the method including:
   generating a reference array of variant data for locations shared between read results to be compared;
   generating hashes over a selected pattern length of positions in the reference array to independently produce non-unique window hashes for base patterns in the read results;
   selecting for comparison window hashes that occur less than a ceiling number of times;
   comparing the selected window hashes to identify common window hashes between the read results; and
   determining a similarity measure for the read results based on the common window hashes.

2. The computer-implemented method of claim 1, wherein the variant data is identified by one selected from sixteen phased pairings and ten unphased pairings.

3. The computer-implemented method of claim 1, wherein the selected pattern length of positions ranges from fifteen to forty bases.

4. The computer-implemented method of claim 1, wherein length of the reference array ranges from one hundred thousand to one million base positions.

5. The computer-implemented method of claim 4, wherein the reference array is ordered by carriers and by carrier positions.

6. The computer-implemented method of claim 4, wherein the pattern length of positions is selected based on the length of the reference array.

7. The computer-implemented method of claim 1, wherein the ceiling number of times ranges from one to ten.

8. The computer-implemented method of claim 1, wherein the similarity measure is determined by a distance formula defined as $$1 - \frac{\text{number of common window hashes}}{\text{number of unique window hashes}}.$$

9. The computer-implemented method of claim 1, further including:
   partitioning the read results into bins;
   comparing the selected window hashes between the read results on a bin-by-bin basis such that selected window hashes for base patterns occurring in corresponding bins in the read results are compared;
   based on the comparing, identifying common window hashes between the corresponding bins; and
   determining a similarity measure for the corresponding bins based on the common window hashes.

10. The computer-implemented method of claim 9, further including:
    requiring that the selected window hashes between the corresponding bins completely match.

11. The computer-implemented method of claim 9, further including:
    based on bin-wise similarity measures, determining a percentage of shared bases between the read results, wherein the percentage of shared bases are determined on a carrier-by-carrier basis; and
    determining inherited traits based on the percentage of shared bases as determined from the bin-wise similarity measures.

12. The computer-implemented method of claim 9, further including:
    based on bin-wise similarity measures, determining a percentage of shared bases between the read results, wherein the percentage of shared bases are determined on a carrier-by-carrier basis; and
    identifying common ancestors and close and distant relatives based on the percentage of shared bases as determined from the bin-wise similarity measures.

13. The computer-implemented method of claim 9, further including:
    based on the bin-wise similarity measures, determining a percentage of shared bases between a given individual's read results and ethnicity-specific read results;
    identifying ethnic ancestry of the given individual based on the percentage of shared bases; and
    for the bin-wise similarity measures, requiring that the selected window hashes between the corresponding bins substantially match.

14. The computer-implemented method of claim 9, wherein the bins are defined for the read results on a carrier-by-carrier basis.

15. The computer-implemented method of claim 9, wherein each bin contains five hundred to thousand variants.

16. The computer-implemented method of claim 9, wherein each bin spans across one hundred thousand to one million bases.

17. The computer-implemented method of claim 9, wherein each bin spans across multiple units.

18. The computer-implemented method of claim 9, further including:
    based on the bin-wise similarity measures, generating a distance tree visualization between the read results.

19. The computer-implemented method of claim 1, wherein the variant data contains those variants that have highest observed frequency.

20. The computer-implemented method of claim 1, further including:

comparing the selected window hashes between the read results on a starting position basis such that selected window hashes for base patterns having same start positions in the read results are compared;

identifying common window hashes between the read results based on the comparing; and determining a similarity measure between the read results based on the common window hashes.

21. The computer-implemented method of claim 20, further including:

based on starting position-wise similarity measures, determining a percentage of shared bases between the read results, wherein the percentage of shared bases are determined on a carrier-by-carrier basis; and determining inherited traits based on the percentage of shared bases as determined from the starting position-wise similarity measures.

22. The computer-implemented method of claim 20, further including:

based on starting position-wise similarity measures, determining a percentage of shared bases between the read results, wherein the percentage of shared bases are determined on a carrier-by-carrier basis; and identifying common ancestors and close and distant relatives based on the percentage of shared bases as determined from the starting position-wise similarity measures.

23. The computer-implemented method of claim 20, further including:

based on the starting position-wise similarity measures, determining a percentage of shared bases between a given individual's read results and ethnicity-specific read results; and identifying ethnic ancestry of the given individual based on the percentage of shared bases.

24. The computer-implemented method of claim 20, further including:

based on the starting position-wise similarity measures, generating a distance tree visualization between the read results.

25. A non-transitory computer readable storage medium impressed with computer program instructions to efficiently compare read results, the instructions, when executed on a processor, implement a method of claim 1:

generating a reference array of variant data for locations shared between read results to be compared;

generating hashes over a selected pattern length of positions in the reference array to independently produce non-unique window hashes for base patterns in the read results;

selecting for comparison window hashes that occur less than a ceiling number of times;

comparing the selected window hashes to identify common window hashes between the read results; and determining a similarity measure for the read results based on the common window hashes.

26. A system including one or more processors coupled to memory, the memory loaded with computer instructions to efficiently compare read results, the instructions, when executed on the processors, implement actions comprising:

generating a reference array of variant data for locations shared between read results to be compared;

generating hashes over a selected pattern length of positions in the reference array to independently produce non-unique window hashes for base patterns in the read results;

selecting for comparison window hashes that occur less than a ceiling number of times;

comparing the selected window hashes to identify common window hashes between the read results; and determining a similarity measure for the read results based on the common window hashes.

27. A computer-implemented method of efficiently comparing sequenced files, the method including:

accessing a first sequenced file and a second sequenced file, wherein the first and second sequenced files contain variants occurring at different carriers and at different carrier positions;

generating a reference array for those carrier positions that are shared between the first and second sequenced files;

based on the reference array, generating a first sequence from the first sequenced file and a second sequence from the second sequenced file;

generating hashes over a selected pattern length of positions in the reference array to independently produce non-unique window hashes for base patterns in the first and second sequences;

selecting for comparison window hashes that occur less than a ceiling number of times;

comparing the selected window hashes to identify common window hashes between the first and second sequences; and determining a similarity measure between the first and second sequences based on the common window hashes.

* * * * *